(12) United States Patent
Zoeller et al.

(10) Patent No.: US 7,629,491 B2
(45) Date of Patent: Dec. 8, 2009

(54) HYDROCARBOXYLATION PROCESS

(75) Inventors: Joseph Robert Zoeller, Kingsport, TN (US); Mary Kathleen Moore, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/426,326

(22) Filed: Jun. 26, 2006

(65) Prior Publication Data

US 2007/0299280 A1  Dec. 27, 2007

(51) Int. Cl.
*C07C 51/10* (2006.01)
*C07C 51/14* (2006.01)

(52) U.S. Cl. .................. 562/521; 562/517; 562/522
(58) Field of Classification Search ................. 562/517, 562/522, 521
See application file for complete search history.

(56) References Cited

U.S. PATENT DOCUMENTS

| | | | |
|---|---|---|---|
| 3,530,155 A * | 9/1970 | Fenton | ........................ 554/129 |
| 3,689,533 A | 9/1972 | Schultz | |
| 3,717,670 A | 2/1973 | Schultz | |
| 3,772,380 A | 11/1973 | Paulik et al. | |
| 3,927,078 A | 12/1975 | Lapporte et al. | |
| 4,046,807 A | 9/1977 | Kuckertz | |
| 4,115,444 A | 9/1978 | Rizkalla | |
| 4,252,741 A | 2/1981 | Porcelli et al. | |
| 4,333,884 A | 6/1982 | Kubbeler et al. | |
| 4,358,411 A | 11/1982 | Porcelli et al. | |
| 4,366,259 A | 12/1982 | Knifton et al. | |
| 4,374,070 A | 2/1983 | Larkins et al. | |
| 4,417,077 A | 11/1983 | Drago et al. | |
| 4,430,273 A | 2/1984 | Erpenbach et al. | |
| 4,484,002 A | 11/1984 | Lin | |
| 4,559,183 A | 12/1985 | Hewleit | |
| 4,629,809 A | 12/1986 | Vanderpool et al. | |
| 5,003,104 A | 3/1991 | Paulik et al. | |
| 5,144,068 A | 9/1992 | Smith et al. | |
| 5,258,549 A | 11/1993 | Pimblett | |
| 5,292,948 A | 3/1994 | Zoeller et al. | |
| 5,298,586 A | 3/1994 | Beevor et al. | |
| 5,380,929 A | 1/1995 | Erpenbach et al. | |
| 5,416,237 A | 5/1995 | Aubigne et al. | |
| 5,442,107 A | 8/1995 | Beevor et al. | |
| 5,488,143 A | 1/1996 | Uhm et al. | |
| 5,510,524 A | 4/1996 | Garland et al. | |
| 5,705,683 A | 1/1998 | Lippert et al. | |
| 5,760,284 A | 6/1998 | Zoeller | |
| 5,866,716 A * | 2/1999 | Schafer et al. | ............... 562/522 |
| 5,900,505 A | 5/1999 | Tustin et al. | |
| 5,922,911 A | 7/1999 | Jones et al. | |
| 5,936,117 A | 8/1999 | Zoeller et al. | |
| 5,977,407 A | 11/1999 | Zoeller | |
| 6,130,355 A | 10/2000 | Jones | |
| 6,211,405 B1 | 4/2001 | Cheung et al. | |
| 6,452,043 B1 | 9/2002 | Zoeller et al. | |
| 6,472,565 B1 | 10/2002 | Bahrmann et al. | |
| 6,667,418 B2 | 12/2003 | Broussard et al. | |
| 6,916,951 B2 * | 7/2005 | Tustin et al. | ................. 560/231 |
| 7,115,774 B2 | 10/2006 | Magna et al. | |
| 2005/0049434 A1 | 3/2005 | Tustin et al. | |
| 2007/0293695 A1 | 12/2007 | Zoeller et al. | |

FOREIGN PATENT DOCUMENTS

| | | |
|---|---|---|
| EP | 0008396 A1 | 5/1980 |
| EP | 0081152 A | 6/1983 |
| EP | 0109212 A | 5/1984 |
| EP | 0087870 B1 | 4/1985 |
| EP | 0096974 B1 | 9/1985 |
| EP | 0153834 | 9/1985 |
| EP | 0338730 A1 | 10/1989 |
| EP | 0391680 | * 10/1990 |
| EP | 0584964 | 3/1994 |
| EP | 0752406 | 1/1997 |
| EP | 0976711 | 2/2000 |
| EP | 0087869 B1 | 11/2006 |
| GB | 2029409 A | 3/1980 |
| JP | 146933 A | 5/2003 |
| WO | 99/54273 A1 | 10/1999 |

OTHER PUBLICATIONS

Wasserscheid, Peter and Keim, Wilhelm, 'Ionic Liquids—New "Solutions" for Transition Metal Catalysis', Angew. Chem. Int. Ed., 2000, 39, 3772-3789.

Howard et al, Catalysis Today, 18 (1993) 325-354.

(Continued)

*Primary Examiner*—Porfirio Nazario-Gonzales
*Assistant Examiner*—Yate' K Cutliff
(74) *Attorney, Agent, or Firm*—Eric D. Middlemas; Bernard J. Graves, Jr.

(57) ABSTRACT

Disclosed is a hydrocarboxylation process for the production of carboxylic acid from olefins wherein an olefin, water, a Group VIII metal hydrocarboxylation catalyst, an onium salt compound are combined in a reaction zone and contacted with carbon monoxide under hydrocarboxylation conditions of pressure and temperature The process does not require or utilize the addition of a hydrogen halide or an alkyl halide exogenous or extraneous to the hydrocarboxylation process.

16 Claims, No Drawings

OTHER PUBLICATIONS

Fujimoto et al, Chemistry Letters (1987) 895-898.
Fujimoto et al, Journal of Catalysis, 133 (1992) 370-382.
Welton, Chemical Reviews, 99, (1999) 2071-2083.
Knifton, J. Catal., 96, (1985) 439-453.
Mizushima et al, Green Chemistry, 3 (2001) 76-79.
Chauvin et al, Chem. Int. Ed. Engl. 34 (1995) 2698-2700.
Yagita et al, Catalysis Letters, 2 (1989) 145-148.
Rangits et al, "Palladium catalysed hydroethoxycarbonylation in imidazolium-based ionic liquids", Journal of Molecular Catalysis A: Chemical 246 (2006) 59-64.
Riisager et al, "First application of supported ionic liquid phase (SILP) catalysis for continuous methanol carbonylation", Chem. Commun. (2006) 994-996.
W. Bertleff, Carbonylation, Ulmann's Encyclopedia of Industrial Chemistry, 6th Edition, vol. 6, Wiley-VCH Verlag GmbH & Co. KGaA, Weinheim, Germany, (2003) p. 473.
W. Rienmenschneider, "Carboxylic Acids, Aliphatic", Ulmann's Encyclopedia of Industrial Chemistry, 6th Edition, vol. 6, Wiley-VCH Verlag GmbH & Co. KGaA, Weinheim, Germany, (2003) p. 473.
Samel et al, "Proprionic Acid and Derivatives", Ulmann's Encyclopedia of Industrial Chemistry, 6th Edition, vol. 30, Wiley-VCH Verlag Gmbh & Co. KGaA, Weinheim, Germany, (2003) p. 261.
Zhao et al, "Ionic liquids: applications in catalysis", Catalysis Today 74 (2002) 157-189.
Riisager et al, "Very Stable and Highly Regioselective Supported Ionic-Liquid-Phase (SILP) Catalysis: Continuous-Flow Fixed-Bed Hydroformylation of Propene", Angew. Chem. Int. Ed. (2005), 44, 815-819.
Mehnert, "Supported Ionic Liquid Catalysis" Chem. Eur. J. (2005), 11, 50-56.
Riisager et al, "Supported Ionic Liqid Phase (SILP) Catalysis: An Innovative Concept for Homegenous Catalysis in Continuous Fixed-Bed Reactors", Eur. J, Inorg. Chem. (2006) 695-706.
Drago et al, "Ionic Attachment as a Feasible Approach to Heterogenizing Anionic Solution Catalysts, Carbonylation of Methanol", Inorganic Chemistry, vol. 20, No. 3, (1981) 641-644.
Haynes et al, "Structure and reactivity of polymer-supported carbonylation catalysts", J. Chem. Soc., Dalton Trans. (2002) 2565-2572.
Welton, "Ionic liquids in catalysis", Coordination Chemistry Reviews 248 (2004) 2459-2477.
Riisager et al, "Stability and Kinetic Studies of Supported Ionic Liquid Phase Catalysts for Hydroformylation of Propene", Ind. Eng. Chem. Res. (2005) 44, 9853-9859.
Copending U.S. Appl. No. 11/424,327, filed on Jun. 15, 2006, Zoeller et al.
Danish application titled "A process for continuous carbonylation by supported ionic liquid-phase catalysis" (Unpublished patent application provided by inventor and believed to be related to Denmark Patent Application No. 2005/00735, filed May 20, 2005, and PCT application Serial No. PCT/DK2006/000275).
Zoeller et al., "Rhodium Catalyzed Carbonylation of Ethylene and Methanol in the Absence of Alkyl Halides Using Ionic Liquids," Organic Reactions Catalysis Society, pp. 1-11 (to be published), (2008).
Article, "Recent advances in processes and catalysts for the production of acetic acid," Applied Catalysis A: General 221 (2001) pp. 253-265.
Office Action dated Sep. 25, 2008 in copending U.S. Appl. No. 11/424,327 filed Jun. 15, 2006.
Yoneda et al., "Recent advances in processes and catalysts for the production of acetic acid," Applied Catalysis A: General 221 (2001) 253-265.
De Blasio, "Activity and Stability of Two Polymer-Supported Rhodium-Based Catalysts for the Vapour Phase Carbonylation of Methanol," Journal of Catalysis, 176, (1998) 253-359.
Sunley et al, "High productivity methanol carbonylation catalysis using iridium The Cativa(TM) process for the manufacture of acetic acid", Catalysis Today, 58, (2000) 293-307.
Copending U.S. Appl. No. 12/060,741 filed Apr. 1, 2008, Zoeller et al.
Office Action dated Aug. 22, 2008 in copending U.S. Appl. No. 12/060,741 filed Apr. 1, 2008, Zoeller et al.
Office Action dated Mar. 6, 2009 in copending U.S. Appl. No. 12/060,741 filed Apr. 1, 2008, Zoeller et al.

* cited by examiner

HYDROCARBOXYLATION PROCESS

FIELD OF THE INVENTION

This invention pertains to a hydrocarboxylation process for the production of carboxylic acids by contacting an olefin with carbon monoxide and water in the presence of a Group VIII metal hydrocarboxylation catalyst and an onium halide compound under hydrocarboxylation conditions of pressure and temperature. The process differs from known processes in that exogenous or extraneous strong acids, such as, hydrogen halide and/or exogenous or extraneous alkyl halide are not required for the conversion of olefins to carboxylic acids.

BACKGROUND OF THE INVENTION

The preparation of carboxylic acids by contacting olefins with carbon monoxide normally requires the use of hazardous and corrosive compounds such as alkyl halides or strong acids, such as hydrogen halides or sulfonic acids (commonly referred to as co-catalysts and/or promoters) or extreme hydrocarboxylation conditions, i.e., extreme pressures and temperatures. Historically, the direct hydrocarboxylation of olefins to carboxylic acids, a process referred to commonly as hydrocarboxylation, entails the use of significant quantities of hazardous and corrosive materials such as alkyl halides (which generate hydrogen halides in situ) or strong acids such as hydrogen halides or sulfonic acids. Such materials commonly are referred to as co-catalysts or promoters. Extreme process pressures and temperatures have been employed in the absence of the corrosive materials mentioned above. Numerous examples of processes utilizing an alkyl halide or strong acid are known in the prior art and are discussed by J. R. Zoeller, U.S. Pat. Nos. 5,760,284; 5,936,117; and 5,977,407 as well as by W. Bertloff, *Carbonylation*, Ulmann's Encyclopedia of Industrial Chemistry, 6$^{th}$ Edition, Vol. 6, Wiley-VCH Verlag GmbH & Co. KGaA, Weinheim, Germany, page 473 (2003); and W. Rienmenschneider, "Carboxylic Acids, Aliphatic", Ulmann's Encyclopedia of Industrial Chemistry, 6$^{th}$ Edition, Vol. 6, Wiley-VCH Verlag GmbH & Co. KGaA, Weinheim, Germany, page 493 (2003). U.S. Pat. No. 6,916,951-B2 and A. Riisager, et. al., *Chemical Communications*, pages. 994-996 (2006) disclose carbonylation processes conducted in the presence of an onium salt and a hydrocarboxylation catalyst wherein gaseous halide such as gaseous methyl iodide is added continuously to a reaction zone.

To avoid the use of a strong acid or alkyl halide in hydrocarboxylation processes for manufacturing carboxylic acids, the use of extreme pressures and temperature or alternative chemistry is necessary. One example of a high pressure and temperature system that does not employ a strong acid is the nickel-catalyzed carbonylation of ethylene to propionic acid that is operated on a commercial scale. This nickel-catalyzed process involves the use of highly toxic nickel carbonyl as the active catalyst at temperatures greater than 270° C. and pressures greater than 186 bar gauge (barg; 2700 pounds per square inch gauge—psig) in a silver lined reactor. This nickel-catalyzed process is described by W. Bertloff, *Carbonylation*, and U.-F. Samel, W. Kohler, A. O. Gamer, and U. Keuser, *Propionic Acid and Derivatives* Ulmann's Encyclopedia of Industrial Chemistry, 6$^{th}$ Edition, Vol. 30, Wiley-VCH Verlag GmbH & Co. KGaA, Weinheim, Germany, p. 261 (2003). Descriptions of other, non-commercial processes may be found in (i) Schafer, Hohn, and Lippert, U.S. Pat. No. 5,866,716, which describes a rhodium/nitrogen heterocycle, e.g., pyridine, catalyst system that, while operating at more moderate temperatures, e.g., 100° C., operates at high pressure, e.g., approximately 100 barg (1470 psig). The process disclosed in U.S. Pat. No. 5,866,716 has some separation difficulties associated with removing the nitrogen heterocycle and produces diethyl ketone by-product. Lippert, Hohn, Schafer, and Hupfer, U.S. Pat. No. 5,705,683 describes an improved nickel-catalyst process that operates at high pressure, e.g., 100 barg, 1470 psig) and temperature, e.g., 200° C. Such high pressures require specialized and costly equipment. These processes also have the disadvantage of producing some diethyl ketone by-product which complicates separation and product purification.

Hydrocarboxylation processes such as, for example, the conversion of ethylene to propionic acid, typically require hydrogen iodide and/or alkyl iodide (e.g., ethyl iodide) to be fed to the reaction zone wherein the hydrocarboxylation reaction occurs. The feed of hydrogen iodide and/or alkyl iodide is problematic since the hydrogen iodide and/or alkyl iodide are corrosive, must be removed from the product and recycled in subsequent distillation steps and, due to its toxicity and volatility, requires very rigorous and expensive process controls. Elimination of the requirement to add significant volumes of alkyl iodide would reduce significantly the costs associated with separation and the expensive control equipment associated with safely handling such a volatile and toxic component.

BRIEF SUMMARY OF THE INVENTION

We have now discovered that the hydrocarboxylation of olefins can be carried out effectively in the absence of strong acids and at mild conditions when the process is operated in the presence of a hydrocarboxylation catalyst, especially Rh, and an onium salt, such as quaternary ammonium or phosphonium salts, that are liquefiable under reaction conditions. We have developed a hydrocarboxylation process which neither utilizes nor requires the introduction or feed of exogenous or extraneous, i.e., exogenous or extraneous to the hydrocarboxylation process, halide compound, e.g., hydrogen halide or an alkyl halide, or strong acids such as sulfonic acids in the production of carboxylic acids. The present invention provides a hydrocarboxylation process for the production of a carboxylic acid which comprises combining in a reaction zone (i) an olefin, (ii) water, (iii) a Group VIII metal hydrocarboxylation catalyst, (iv) an onium salt compound and (v) carbon monoxide under hydrocarboxylation conditions of pressure and temperature, wherein neither a hydrogen halide nor an alkyl halide exogenous or extraneous to the hydrocarboxylation process is added or supplied to the reaction zone. The present process provides a means for the elimination of significant quantities of a strong acid or alkyl halide while still operating under relatively middle conditions, especially when using the preferred rhodium hydrocarboxylation catalyst. The process of the invention produces less carboxylic acid ester co-product compared to known processes for the conversion of olefins to carboxylic acids wherein an alkyl halide such as ethyl iodide is fed to the reaction zone. Furthermore, the present process does not generate detectable diethyl ketone by-products.

DETAILED DESCRIPTION

The olefin feedstock reactant that may be employed in the hydrocarboxylation process may contain from 2 to about 12 carbon atoms to produce a carboxylic acid containing 3 to about 12 carbon atoms. The olefin feedstock preferably is an α-olefin. The olefin feedstock preferably is selected from lower olefins such as ethylene which yields propionic acid and propylene which yields butyric and isobutyric acids. Depending on the mode of operation of the process and the particular olefin feedstock employed, the olefin feedstock compound may constitute about 1 to about 90 weight percent of the reaction medium or solution when using liquid olefin feedstocks, i.e., the total weight of the contents of the reaction zone, wherein a mixture of olefin and water is contacted with carbon monoxide in the presence of a Group VIII metal hydrocarboxylation catalyst and an onium salt compound. The term "weight percent", as used herein, is based on the total weight of the contents of the reaction zone. When using the preferred gaseous olefins, such as ethylene and propylene, the concentration of olefin is a function of pressure and the onium salt used in the process because olefin solubility varies with the nature of onium salt and pressure.

The process of the present invention is carried out in the presence of water. The concentrations of water in the reaction medium or solution may vary during the operation of the process, particularly when operated in a batch mode. The concentration of water may vary from about 1 to about 50 weight percent at the start of the process reaction in a batch operation to about 0.1 to about 20 weight percent in the final reaction mixture in either a continuous or batch process. The process preferably is operated using at least a slight stoichiometric excess (with reference to the olefin feedstock) of water. Operation of the process in the absence of sufficient water results in the formation of excessive amounts ester by-product(s).

The Group VIII metal hydrocarboxylation catalyst may be selected from a variety of compounds of the metals in Groups 8, 9, and 10, i.e., Fe, Ru, Os, Co, Rh, Ir, Ni, Pd and Pt of the Periodic Table of the Elements (commonly referred to as the "Group VIII" metals). The above group numbering is in accordance with the 1984 revision to the Periodic Table by the International Union of Pure and Applied Chemistry. Co, Rh, Ir, Ni, and Pd and compounds and complexes thereof are preferred with compounds and complexes of Rh being especially preferred. Any form of these metals may be used and they may be used as single components or in combination with one another. The Group VIII metal hydrocarboxylation catalysts may be employed in combination with promoters or co-catalysts such as alkali metal compounds, group 6 metal (Cr, Mo, W) compounds, alkaline earth metals compounds and compounds of zinc, tin and lanthanide metals. Additional ligands such tertiary amines and phosphines, i.e., unquarternized or non-protonated amines and phosphines, also may be present although they are not necessarily required for efficient operation of the process. The Group VIII metal hydrocarboxylation catalysts typically are used in concentrations between about 0.0001 mol to about 1 mol per kg of reaction medium or solution. The more active of the Group VIII metal hydrocarboxylation catalysts typically are used in concentrations of about 0.001 to about 0.1 mol per kg of reaction medium or solution.

The hydrocarboxylation process of the present invention is carried out in the presence of an onium salt comprising a cation selected from quaternary atoms or radicals such as quaternary ammonium, quaternary phosphonium, trialkyl sulfonium, and alkylated sulfoxides. The onium salt compound may be functional and includes protonated forms of the atoms or radicals, especially protonated forms of various tertiary amines and tertiary phosphines. The onium salt may contain any number of carbon atoms, e.g., up to about 60 carbon atoms, and also may contain one or more heteroatoms. The tri- and tetra-alkyl quaternary ammonium and phosphonium salts typically contain a total of about 5 to 40 carbon atoms.

Examples of quaternary ammonium and phosphonium salts include salts of cations having the formula

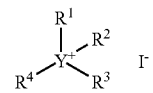

wherein $R^1$, $R^2$, $R^3$, and $R^4$ are independently selected from alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms; and Y is N or P. The quaternary ammonium salts also may be selected from salts of aromatic, heterocyclic onium cations having the formula

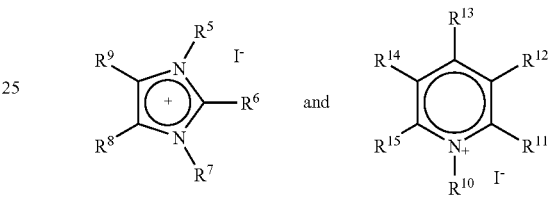

wherein at least one ring atom is a quaternary nitrogen atom and $R^6$, $R^8$, $R^9$, $R^{11}$, $R^{12}$, $R^{13}$, $R^{14}$, and $R^{15}$ are independently selected from hydrogen, alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms; and $R^5$, $R^7$, and $R^{10}$ are independently selected from alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms.

Examples of specific ammonium salts include tetrapentylammonium iodide, tetrahexylammonium iodide, tetraoctylammonium iodide, tetradecyl-ammonium iodide, tetradodecylammonium iodide, tetrapropylammonium iodide, tetrabutylammonium iodide, ethyltrioctylammonium iodide, ethyltributylammonium iodide, N-octylquinuclidinium iodide, N,N'-diethyl-N,N'-dihexadecylpiperazinium diiodide, diethyl-hexadecyl-[3-pyrrolidinylpropyl]ammonium iodide, N,N,N,N',N',N'-hexa(dodecyl)octane-1,8-diammonium diiodide, N,N,N,N',N',N'-hexa(do-decyl)butane-1,4-diammonium diiodide; imidazolium iodides such as 1-butyl-3-ethylimidazolium iodide, 1,3-diethylimidazolium iodide, 1,3-diethyl-4-methyl-imidazolium iodide, 1,3,diethyl-2,4,5-trimethylimidazolium iodide; pyridinium iodides such as N-octylpyridinium iodide, N-ethylpyridinium iodide, N-ethyl-2-picolinium iodide, N-ethyl-3-picolinium iodide, N-ethyl-4-picolinium iodide, N-ethyl-5-ethyl-2-methyl-pyridinium iodide, N-ethyl-3,4-lutidinium iodide; N-ethyl quinolinium iodide, N-ethyl isoquinolinium iodide or mixtures thereof. Preferred quaternary ammonium iodides include 1-butyl-3-ethylimidizolium iodide, N-ethylpyridinium iodide, N-ethyl-5-ethyl-2-methyl-pyridinium iodide, and 1,3-diethylimidazolium iodide. Exemplary phosphonium compounds include tetraoctylphosphonium iodide, tetrabutylphosphonium iodide, triphenyl(hexyl)-phosphonium iodide, triphenyl(octyl)-phosphonium iodide, tribenzyl(octyl)phosphonium iodide, tribenzyl(dodecyl)phosphonium iodide, triphenyl(decyl)-phosphonium iodide, triphenyl(dodecyl)phosphonium iodide, tetrakis(2-methylpropyl)phosphonium iodide, tris(2-methylpropyl)(butyl)phosphonium iodide, triphenyl(3,3-dimethylbutyl)phosphonium iodide, triphenyl(3-methylbutyl)phos-phonium iodide, tris(2-methylbutyl)(3-methylbutyl)phosphonium iodide, triphenyl[2-trimethylsilylethyl]phosphonium iodide, tris(p-chlorophenyl)-(dodecyl)phosphonium iodide, hexyltris(2,4,6-trimethylphenyl)phosphonium iodide, tetradecyltris(2,4,6-trimethylphenyl)phosphonium iodide, dodecyltris(2,4,6-trimethylphenyl)phosphonium iodide, ethyltriocytlphosphonium iodide, ethyltributylphosphonium iodide, ethyltricyclohexylphosphonium iodide, and the like. Preferred phosphonium iodides include ethyltriphenylphosphonium iodide, ethyltributylphosphonium iodide, ethyltriocytlphosphonium iodide, and butyltridodecylphosphonium iodide.

The onium salt also may be a polymer containing quaternary nitrogen groups such as polymers and copolymers derived in whole or part from (or containing polymerized residues of) 2- or 4-vinyl-N-alkylpyridinium halides or 4-(trialkylammonium)styrene halides. The most preferred onium salts comprise N-alkylpyridinium halides and N,N'-(or 1,3-)dialkylimidazolium halides wherein the alkyl groups contain 1 to about 4 carbon atoms. The iodide salts are especially preferred. The onium salts may consist of one or more quaternary cations and/or one or more anions. The anion(s) of the onium salts may be selected from a wide variety of species such as halides, carboxylates, tetraflouroborate, hexahalophosphates, bis (trifluoro-methanesulfonyl)amide [(CF3SO2)2N-], and anionic metal complexes such as (CO)4Co—, trihalozincates, (ZnX3-, X=F,Cl,Br, I), trichlorostannates (SnCl3-) diododicarbonylrhodate (I) and diiododicarbonyliridate (I) and may be mixtures of anions. However, the most useful anions are the halides and carboxylates or mixtures thereof both from ease of manufacture and function in the hydrocarboxylation process. The iodide salts are especially preferred. The onium salt typically constitutes about 5 to about 95 weight percent of the reaction medium or solution depending on the particular onium salt employed and the mode of operation of the hydrocarboxylation process.

The onium salts may be prepared according to various procedures known in the art. The most efficient method for preparing the preferred halide salts is to simply alkylate or protonate the amine or phosphine precursor with an alkyl or hydrogen halide. Due their ease of preparation and availability of the amine and phosphine precursors, the most preferred onium salts for a liquid phase operation are selected from the group of salts consisting of quaternary ammonium and phosphonium halides, with the most preferred being iodide salts derived from pyridine and imidazole derivatives. The following example illustrates one technique for the preparation of the preferred onium salt—1,3-dimethylimidazolium iodide: To a single neck, 2-liter flask equipped with magnetic-stir bar, nitrogen inlet, condenser and an addition flask, was added 136 grams of 1-ethylimidazole (1.41 moles) and 800 ml of ethyl acetate. Iodoethane (522 grams, 3.54 moles) was added dropwise over a period of 1 hour to control the exotherm. The reaction mixture was stirred overnight at room temperature. The liquid was decanted and the solids were washed with ethyl acetate and dried on a rotary evaporator for 1 hour at 60° C. under 0.1 mbar of pressure. The 1,3-diethylimidazolium iodide product (358 g, 1.41 moles, 100% mass yield) was a crystalline solid and was spectroscopically pure by NMR.

The carbon monoxide may be fed to the reaction or hydrocarboxylation zone either as purified carbon monoxide or as carbon monoxide including other gases. The carbon monoxide need not be of high purity and may contain from about 1% by volume to about 100% by volume carbon monoxide, and preferably from about 70% by volume to about 99% by volume carbon monoxide. The remainder of the gas mixture may include such gases as nitrogen, hydrogen, water and parafinic hydrocarbons having from one to four carbon atoms. Although hydrogen is not part of the reaction stoichiometry, hydrogen may be useful in maintaining optimal catalyst activity. Therefore, the preferred ratio of carbon monoxide to hydrogen is in the range of about 99:1 to about 2:1, but ranges with even higher hydrogen levels are also useful.

The hydrocarboxylation conditions of pressure and temperature may vary significantly depending upon various factors such as, for example, the mode of operation, the Group VIII catalyst employed, the process apparatus utilized and the degree of conversion of the olefin feedstock that is desired. For example the process generally may be operated under a total pressure ranging from atmospheric pressure to 250 bar gauge (barg; 3700 pounds per square inch gauge—psig). However, total pressures in the range of about 5 to about 100 barg (72.6 to 1450 psig) are more typical with pressures in the range of about 10 to about 80 barg being preferred when using the preferred rhodium as the Group VIII metal hydrocarboxylation catalyst. The process temperature may range from about 50 to about 300° C. although temperatures in the range of about 150 to about 250° C. are more typical.

The carbon monoxide pressure may be from atmospheric pressure to about 250 barg (3700 psig). However, high pressures are not required and are disadvantageous from an equipment cost perspective. The carbon monoxide pressure typically is in the range of about 2 bar to about 50 barg (29 to 750 psig) with CO partial pressures in the range or about 2 to about 40 bar (29 to 600 psig) being the most useful. The olefin pressure is dependent upon the nature of the olefin since the lower, most useful olefins are gases under operating conditions whereas the higher olefins are liquids. For the gaseous olefins such as ethylene and propylene which represent the preferred application, the olefin partial pressure typically is in the range of about 2 to about 100 barg (29 to 1450 psig). Olefin partial pressures of about 2 to about 40 barg (29 to 580 psig) are preferred when the olefin feedstock is ethylene or propylene. In processes using gaseous olefins, the CO:olefin mole ratio may be in the range of about 10:1 to about 1:10 while CO:olefin mole ratios of about 2:1 to about 1:2. Mole ratios approaching the stoichiometric quantity (1:1) are most preferred.

When the olefin feedstock is a liquid, e.g., C-5 to C-12 olefins, the concentration may vary depending upon the mode of operation and specific olefin employed. However, in a batch mode of operation, the starting concentration of liquid olefin typically is in the range of about 1 to about 75 weight percent based on the total weight of the reaction medium or solution. Initial concentrations of liquid olefin are in the range of about 10 to about 50 weight percent (same basis). When operated in a continuous mode, the concentration of olefin in the reaction medium is in the range of about 0.01 to about 50 weight percent with concentrations of about 0.1 to about 10 weight percent in the product effluent. In an alternative mode, wherein the reaction is run in a biphasic process and the olefin may function as both a reactant and an extractant for the product, concentrations in the layer (which is to be removed) may be extremely high, e.g., as high as 95 weight percent, but more typically in the range of about 20 to about 80 weight percent when used in this mode. The product concentration depends on the olefin feedstock and water concentrations and may consist of a mixture of carboxylic acid isomers.

In the hydrocarboxylation process provided by the present invention neither hydrogen halide nor an alkyl halide exogenous or extraneous to the hydrocarboxylation process is added or supplied to the reaction zone, i.e., fresh hydrogen halide and/or fresh alkyl halide are not fed to the reaction zone of the process. The terms "exogenous" or "extraneous", as used herein, is not intended to include minor amounts, i.e., minor as compared to known processes, of such halides, for example, ethyl iodide, which may form in situ during operation of the process by reaction of a feedstock compound, with a halide anion of the onium salt compound and which may be recovered and recycled to the reaction zone. In continuous operation of the hydrocarboxylation process, for example, a low boiling stream is recovered from the product recovery and refining section of the process. This low boiling stream normally is recycled to the reaction zone of the hydrocarboxylation process.

The hydocarboxylation process provided by the present invention provides a means for preparing carboxylic acids from olefins using a mixture or solution of a Group VIII metal hydrocarboxylation catalyst and an onium salt, preferably an ammonium or phosphonium iodide. The onium salt and Group VIII metal catalyst in this invention are non-volatile, permitting easy product separation without loss of catalyst or onium salt. The process may be carried out using any of a variety of operational modes. The following process modes of operation are representative:

(1) A process comprising the steps of:
  (i) feeding to a reaction zone (i) an olefin, (ii) water, (iii) a Group VIII metal hydrocarboxylation catalyst, (iv) an onium salt compound and, optionally, an inert solvent to provide a reaction zone liquid and feeding carbon monoxide to the reaction zone liquid under hydrocarboxylation conditions of pressure and temperature; and
  (ii) removing from the reaction zone a crude liquid product comprising a carboxylic acid, unreacted olefin, water, Group VIII metal hydrocarboxylation catalyst, onium salt compound, optional inert solvent and carbon monoxide;
  wherein neither a hydrogen halide nor an alkyl halide exogenous or extraneous to the hydrocarboxylation process is added to the reaction zone.

(2) A process comprising the steps of:
  (i) feeding (i) an olefin, (ii) water, and carbon monoxide to a reaction zone containing a solution comprising a Group VIII metal hydrocarboxylation catalyst and an onium salt compound to provide a reaction zone liquid maintained under hydrocarboxylation conditions of pressure and temperature wherein the temperature of the reaction zone is maintained above the dew point of the carboxylic acid; and
  (ii) removing from the reaction zone a crude gaseous product comprising carboxylic acid, olefin, water and carbon monoxide.
  wherein neither a hydrogen halide nor an alkyl halide exogenous or extraneous to the hydrocarboxylation process is added to the reaction zone.

(3) A process comprising the steps of:
  (i) feeding gaseous olefin, gaseous water and carbon monoxide to a reaction zone containing a heterogeneous or solid Group VIII metal hydrocarboxylation catalyst and a heterogeneous or solid onium salt compound (1) deposited on a catalyst support material or (2) in the form of a polymeric material containing quaternary nitrogen groups wherein the reaction zone is maintained under hydrocarboxylation conditions of pressure and temperature wherein the temperature of the reaction zone is maintained above the dew point of the carboxylic acid; and
  (ii) removing from the reaction zone a crude gaseous product comprising carboxylic acid, unreacted olefin, water and carbon monoxide.
  wherein neither a hydrogen halide nor an alkyl halide exogenous or extraneous to the hydrocarboxylation process is added to the reaction zone.

Mode (1) is carried out using a homogeneous liquid reaction medium or reaction zone maintained at a temperature of about 100 to about 250° C. and a total pressure of about 5 to about 80 barg. When operating in a continuous mode, the liquid reaction medium typically comprises about 0.1 to about 15 weight percent water, about 25 to about 75 weight percent carboxylic acid product, about 15 to about 75 weight percent onium salt and about 0 to about 75 weight percent of an optional inert solvent. The typical weight of the olefin present will depend on the nature of the olefin. In continuous operation using liquid olefins, the liquid olefin typically comprises about 0.5 to about 25 weight percent of the reaction medium, but may reach 75 weight percent in operations wherein the olefin is used as the optional reaction solvent. With gaseous olefins, such as ethylene and propylene, the concentration is a function of the nature of the onium salt and pressure and can be as low as 0 weight percent where it is operating as a biphasic reaction, or can be as high as 25 weight percent. However, typically, the olefin concentration with gaseous olefins will comprise 0 to about 25 weight percent of the reaction mixture within a continuous process. The optional inert solvent preferably is a carboxylic acid, preferably the carboxylic acid corresponding to the hydrocarboxylation product, e.g., propionic acid when the hydrocarboxylation product is propionic acid. Carboxylic acid product is recovered from the crude liquid product removed from the reaction zone. The remainder of the crude product comprises a low boiling fraction comprising unreacted olefin and a high boiling fraction comprising Group VIII metal hydrocarboxylation catalyst, onium salt compound and optional inert solvent. Normally some or all of the low boiling and high boiling fractions are recovered from the crude liquid product and recycled directly or indirectly to the reaction zone. Thus, continuous operation of mode (1) of the process may, and typically does, include the steps of:
  (iii) refining the crude liquid product to recover (1) carboxylic acid product, (2) a low boiling fraction comprising unreacted olefin and (3) a high boiling fraction comprising Group VIII metal hydrocarboxylation catalyst, onium salt compound and optional inert solvent; and
  (iv) recycling the low boiling and high boiling fractions to the reaction zone.

Mode (2) is carried out using a liquid reaction medium or liquid reaction zone maintained at a temperature above the dew point of the carboxylic acid product, which enables the carboxylic acid product, either by itself or as component in a mixture of gases, be removed from the reaction zone in the gas phase. Since the dew point is a complex function of dilution (particularly with respect to non-condensable gases such as unreacted carbon monoxide, hydrogen, or inert diluent gas, crude product composition, and pressure, the process may still be operated over a wide range of temperatures, provided the temperature exceeds the dew point of the product effluent. The term "dew point", as used herein, means the temperature, at a given pressure, at which a gas is saturated with respect to its condensable components and at which condensation occurs. The dew point of the products of the present invention may be calculated by methods well known to those skilled in the art, for example, as described in Perry's Chemical Engineer's Handbook, 6$^{th}$ ed, (McGraw-Hill), pp. 13-25 through 13-126. Dew points for single product or complex mixtures may be calculated using commercially available engineering computer programs, such as Aspen®, also well-known to those skilled in the art. In practice, the process typically operates at a temperature of about 100 to about 250° C. Other examples of temperature ranges over which the Mode (2) process may operate include about 120 to about 240° C. and about 150 to about 240° C. The total pressure of the reaction zone typically is maintained in the range of about 1 to about 80 barg or, in another example, about 10 to about 50 barg. The liquid reaction medium may comprise a solution of the Group VIII metal compound in a melt of the onium salt compound or it may comprise a solution of the Group VIII metal compound and the onium salt compound in a high-boiling, i.e., substantially non-volatile under reaction conditions, solvent. Examples of such high-boiling solvents include sulfoxides and sulfones, e.g., dimethyl sulfoxide and sulfolane; amides, e.g., N-methyl-2-pyrrolidinone (NMP), dimethylacetamide, $C_6$ to $C_{30}$ carboxylic acids; aromatic hydrocarbons, e.g., 2-methylnaphthalene; and high-boiling, saturated hydrocarbons, e.g., decalin, dodecane. While the Mode (2) reaction nominally is a vapor phase process and contains little or no detectable hydrocarboxylation feedstock or product, the liquid reaction medium or reaction zone typically contains at least a portion of the olefin feedstock and carboxylic acid product as a solution. Typically, the reaction medium or zone comprises about 1 to about 10 weight percent of olefin feedstock when using a liquid olefin feedstock, about 1 to about 50 weight percent carboxylic acid product, about 10 to about 50 weight percent onium salt and 0 to about 75 weight percent high-boiling solvent. Normally-liquid olefins may be fed to the Mode (2) process either as a vapor or liquid. A liquid feed is converted to a vapor within the reaction zone or preferably in a preheated section of the process apparatus. The effluent from the Mode (2) process is a vapor typically comprised of carboxylic acid product, unconverted olefin feedstock and carbon monoxide. Operation of the hydrocarboxylation process of the present invention according to Mode (2) is further described in U.S. Pat. No. 6,916,951-B1. Any onium salt, catalyst, optional inert solvent, olefin feedstock, or low boiling components or intermediates present in the gaseous product removed from the reaction zone may be separated during product recovery/purification and returned to the reaction zone. Continuous operation of Mode (2) of the process typically includes the steps of:

(iii) refining the crude gaseous hydrocarboxylation product to recover (1) carboxylic acid product and (2) a low boiling fraction comprising unreacted olefin; and (iv) recycling the low boiling fraction to the reaction zone.

Operation of the process according to Mode (3) is somewhat similar to the Mode (2) operation except that both the Group VIII metal hydrocarboxylation catalyst and the onium compound are in heterogeneous forms. The Group VIII metal hydrocarboxylation catalyst may be deposited on a catalyst support material such as carbon or an inorganic oxide such as alumina or silica according to known procedures. Alternatively, the onium salt may be generated from polymers containing a quaternary, or quaternizable, phosphine or amine. For example, a variety of 4-vinyl pyridine polymers and copolymers are available, and may be quaternized or protonated with alky halides or hydrogen halides to generate heterogeneous onium salts. Further, polymers of N-methyl-4-vinylpyridium chloride are commercially available and may be used as is or preferably exchanged with iodide by well known means to form the iodide salt. The heterogeneous onium compound may comprise (1) an onium salt compound deposited on a catalyst support material or (2) of a polymeric material containing quaternary nitrogen groups. Examples of such polymeric onium compounds include polymers and copolymers of vinyl monomers which contain quaternary nitrogen (ammonium) groups. Polymers and copolymers derived from 2- and 4-vinyl-N-alkylpyridinium halides, e.g., poly(4-vinyl-N-methylpyridinium iodide), are specific examples of such polymeric onium salt compounds. In the Mode (3) operation the reaction zone is maintained at a temperature above the dew point of the carboxylic acid product. Thus, the hydrocarboxylation conditions of pressure and temperature employed in Mode (3) are similar to those used in Mode (2). Vapor phase operation wherein an alkyl halide is used is described in U.S. Pat. No. 6,452,043-B1, U.S. Patent No. 2005/0049434-A1 and A. Riisager, et. al., Chemical Communications, pp. 994-996 (2006). Any onium salt, catalyst, optional inert solvent, unreacted olefin, or low boiling components or intermediates entrained in the vapor effluent product normally are separated during purification and returned to the reaction zone. Continuous operation of the Mode (3) process typically includes the steps of:

(iii) refining the crude gaseous product to recover (1) carboxylic acid product and (2) a low boiling fraction comprising unreacted olefin; and (iv) recycling the low boiling fraction to the reaction zone.

EXAMPLES

The process of the present invention is further illustrated by the following examples wherein the percentages are by weight except for the hydrogen/carbon monoxide and the olefin/hydrogen/carbon monoxide mixtures wherein the percentages are by mole. The experiments described in the examples were carried out in an autoclave constructed of Hastelloy® C-276 alloy. Gaseous materials were fed to the autoclave through a high-speed stirrer that provided agitation to the reaction zone.

Example 1

To a 300 mL autoclave equipped with a condenser to return liquid to the autoclave and a gas purge at the top of the condenser, was added 0.396 g (1.5 mmol) of $RhCl_3 \cdot 3H_2O$, 117.5 g (0.50 mol) of N-ethylpyridinium iodide, and 36.0 g (2.0 mol) of water. The autoclave was sealed, flushed with nitrogen, and then pressurized to 17.2 barg (250 psig) with 5% hydrogen in CO. A purge of 1.0 mol/hour through the condenser cooled to 10° C. was established. The reaction mixture was heated to 190° C. maintaining the gas purge pressure at 17.2 barg (250 psig) with 5% hydrogen in carbon monoxide. Upon reaching 190° C. the gas feed was switched to a mixture of 50% CO: 45% ethylene; 5% hydrogen and the pressure adjusted to 51.7 barg (750 psig) using a mixture consisting of 50% CO, 45% ethylene and 5% hydrogen. The temperature and pressure were maintained for 5 hours using the 50% CO, 45% ethylene, 5% hydrogen gas mixture to maintain pressure. After 5 hours, the reaction mixture was cooled, vented, and the crude product transferred to a sample bottle. GC analysis of the crude product showed that it contained 0.07% ethanol, 1.60% ethyl propionate, and 32.54% propionic acid. This represents 0.555 moles of propionic acid, 0.020 moles of ethyl propionate, and 0.0019 moles of ethanol. No ethyl iodide was detected in the product by GC analysis.

Example 2

To a 300 mL autoclave equipped with a condenser to return liquid to the autoclave and a gas purge at the top of the condenser, was added 0.789 g (3.0 mmol) of $RhCl_3 \cdot 3H_2O$, 122 g (0.545 mol) of N,N'-dimethylimidazolium iodide, and 27.0 g (1.5 mol) of water. The autoclave was sealed, flushed with nitrogen, and then pressurized to 17.2 barg (250 psig) with 5% hydrogen in CO. A purge of 1.0 mol/hour through the condenser cooled to 10° C. mixture was established. The mixture was heated to 190° C. maintaining the gas purge pressure at 17.2 barg (250 psig) with 5% hydrogen in carbon monoxide. Upon reaching 190° C. the gas feed was switched to a mixture of 50% CO, 45% ethylene and 5% hydrogen and the pressure adjusted to 31.0 barg (450 psig) using the mixture of 50 mol % CO: 45 mol % ethylene and 5 mol % hydrogen. The temperature and pressure were maintained for 8 hours using the 50% CO, 45% ethylene, 5% hydrogen gas mixture as needed to maintain pressure. After 8 hours, the reaction mixture was cooled, vented, and the crude product transferred to a sample bottle. GC analysis of the crude product showed that it contained 1.04% ethyl propionate and 39.53% propionic acid. This represents 1.153 moles of propionic acid and 0.018 moles of ethyl propionate. No ethyl iodide was detected in the product by GC analysis.

Example 3

To a 300 mL autoclave equipped with a condenser to return liquid to the autoclave and a gas purge at the top of the condenser, was added 0.789 g (3.0 mmol) of $RhCl_3 \cdot 3H_2O$, 122 g (0.484 mol) of N,N'-diethylimidazolium iodide and 27.0 g (1.5 mol) of water. The autoclave was sealed, flushed with nitrogen, and then pressurized to 17.2 barg (250 psig) with 5% hydrogen in CO. A purge of 1.0 mol/hour through the condenser cooled to 10° C. was established. The mixture was heated to 190° C. maintaining the gas purge pressure at 17.2 barg (250 psig) with 5% hydrogen in carbon monoxide. Upon reaching temperature the gas feed was switched to a mixture of 50% CO, 45% ethylene and 5% hydrogen and the pressure adjusted to 31.0 barg (450 psig) using the mixture of 50% CO, 45% ethylene and 5% hydrogen. The temperature and pressure were maintained for 3.5 hours using the 50 mol % CO, 45 mol % ethylene, 5 mol % hydrogen gas mixture as needed to maintain pressure. After 3.5 hours, the reaction mixture was cooled, vented, and the crude product transferred to a sample bottle. GC analysis of the crude product showed that it contained 0.47% ethanol, 0.19% ethyl propionate, and 11.00% propionic acid. This represents 0.244 moles of propionic acid, 0.004 moles of ethyl propionate, and 0.014 moles of ethanol. No ethyl iodide was detected in the product by GC analysis.

Example 4

To a 300 mL autoclave equipped with a condenser to return liquid to the autoclave and a gas purge at the top of the condenser, was added 0.789 g (3.0 mmol) of $RhCl_3 \cdot 3H_2O$, 101 g (0.40 mol) of N,N'-diethylimidazolium iodide and 27.0 g (1.5 mol) of water. The autoclave was sealed, flushed with nitrogen, and then pressurized to 17.2 barg (250 psig) with 5% hydrogen in CO. A purge of 1.0 mol/hour through the condenser cooled to 10° C. was established. The mixture was heated to 190° C. maintaining the gas purge pressure at 17.2 barg (250 psig) of 5% hydrogen in carbon monoxide. Upon reaching 190° C. the gas feed was switched to a mixture of 50% CO, 45% ethylene and 5% hydrogen and the pressure adjusted to 51.7 barg (750 psig) using the mixture of 50% CO, 45% ethylene and 5% hydrogen. The temperature and pressure were maintained for 6 hours using the 50 mol % CO: 45 mol % ethylene; 5 mol % hydrogen gas mixture as needed to maintain pressure. GC analysis of the crude product after 6 hours of reaction time showed that it contained 2.13% ethyl propionate, and 39.17% propionic acid. This represents 0.994 moles of propionic acid and 0.039 moles of ethyl propionate. No ethanol or ethyl iodide were detected in the product by GC analysis.

Example 5

To a 300 mL autoclave equipped with a condenser to return liquid to the autoclave and a gas purge at the top of the condenser, was added 0.396 g (1.5 mmol) of $RhCl_3 \cdot 3H_2O$, 102.4 g (0.20 mol) of methyl triocytyl phosphonium iodide, and 27.0 g (1.5 mol) of water. The autoclave was sealed, flushed with nitrogen, and then pressurized to 17.2 barg (250 psig) with 5% hydrogen in CO. A purge of 1.0 mol/hour was established through the condenser cooled to 10° C. The mixture was heated to 190° C. maintaining the gas purge pressure at 17.2 barg (250 psig) of 5% hydrogen in carbon monoxide. Upon reaching 190° C. the gas feed was switched to a mixture of 50% CO, 45% ethylene and 5% hydrogen and the pressure adjusted to 51.7 barg (750 psig) using the mixture of 50% CO, 45% ethylene and 5% hydrogen. The temperature and pressure were maintained for 5 hours using the 50% CO, 45% ethylene and 5% hydrogen gas mixture as needed to maintain pressure. GC analysis of the crude product after 5 hours of reaction time had elapsed showed that it contained 12.96% propionic acid. This represents 0.253 moles of propionic acid. No ethanol, ethyl propionate, or ethyl iodide were detected by GC analysis.

Example 6

To a 300 mL autoclave equipped with a condenser to return liquid to the autoclave and a gas purge at the top of the condenser, was added 0.396 g (1.5 mmol) of $RhCl_3 \cdot 3H_2O$, 101 g (0.40 mol) of N,N'-diethylimidazolium iodide, 35.0 g (0.5 mol) of 1-pentene and 9.0 g (0.5 mol) of water. The autoclave was sealed, flushed with nitrogen, and then pressurized to 17.2 barg (450 psig) with 5% hydrogen in CO. A purge of 1.0 mol/hour was established through the condenser cooled to 10° C. The mixture was heated to 190° C. maintaining the gas purge pressure at 31.0 barg (450 psig) of 5% hydrogen in carbon monoxide. Upon reaching 190° C. the gas feed was switched to 100% CO and the pressure adjusted to 51.7 barg (750 psig) with 100% CO. The temperature and pressure were maintained for 8 hours using 100% CO as needed to maintain pressure. After 8 hours, the reaction was cooled, vented, and the crude product transferred to a sample bottle. The crude product formed two layers, the upper layer weighing 18.74 g and the lower layer weighing 134.21 g. Liquid chromatographic analysis of the two layers for C-6 carboxylic acids showed that the upper layer contained 3.16% 2-ethylbutanoic acid, 12.07% 2-methylpentanoic acid, and 17.80% hexanoic acid, while the bottom layer contained 0.51% 2-ethylbutanoic acid, 1.57% 2-methylpentanoic acid, and 2.82% hexanoic acid. This represents a total weight of 12.78 g for the sum of all the C-6 carboxylic acids, representing 0.11 moles of C-6 carboxylic acid.

Comparative Example 1

To a 300 mL autoclave equipped with a condenser to return liquid to the autoclave and a gas purge at the top of the condenser, was added 0.789 g (3.0 mmol) of $RhCl_3 \cdot 3H_2O$, 122 g (0.545 mol) of N,N'-dimethylimidazolium iodide, 27.0 g (1.5 mol) of water, and 15.6 g (0.1 mol) of ethyl iodide. The autoclave was sealed, flushed with nitrogen, and then pressurized to 17.2 barg (250 psig) with 5% hydrogen in CO. A purge of 1.0 mol/hour was established through the condenser cooled to 10° C. The mixture was heated to 190° C. maintaining the gas purge pressure at 17.2 barg (250 psig) of 5% hydrogen in carbon monoxide. Upon reaching 190° C. the gas feed was switched to a mixture of 50% CO, 45% ethylene and 5% hydrogen and the pressure adjusted to 31.0 barg (450 psig) using a mixture of 50% CO, 45% ethylene; 5% hydrogen. The temperature and pressure were maintained for 5 hours using the 50% CO, 45% ethylene, 5% hydrogen gas mixture as needed to maintain pressure. After 5 hours, the reaction mixture was cooled, vented, and the crude product transferred to a sample bottle. GC analysis of the crude product showed that it contained 0.5% water, 0.53% ethyl iodide, 16.69% ethyl propionate, and 26.39% propionic acid. This represents 0.890 moles of propionic acid and 0.408 moles of ethyl propionate. This comparative example demonstrates that the inclusion of ethyl iodide in the initial reaction mixture results in a significant reduction in selectivity to the desired carboxylic acid with much larger quantities of ethyl propionate being generated.

The invention has been described in detail with particular reference to preferred embodiments thereof, but it will be understood that variations and modifications can be effected within the spirit and scope of the invention.

We claim:

1. Process for the production of a carboxylic acid which comprises combining in a reaction zone (i) an olefin, (ii) water, (iii) a Group VIII metal hydrocarboxylation catalyst, (iv) an onium halide salt compound and (v) carbon monoxide under hydrocarboxylation conditions of pressure and temperature, wherein a halide compound, other than the onium halide salt, exogenous or extraneous to the hydrocarboxylation process is not added or supplied to the reaction zone.

2. Process according to claim 1 wherein the olefin contains 2 to about 12 carbon atoms, the onium halide salt is a quaternary ammonium iodide or a quaternary phosphonium iodide, the Group VIII metal hydrocarboxylation catalyst is rhodium or a rhodium compound and the hydrocarboxylation conditions of pressure and temperature comprise total pressures of about 5 to about 100 barg and temperatures of about 50 to about 300° C.

3. Process according to claim 2 wherein the onium halide salt is an imidazolium iodide or a pyridinium iodide and the hydrocarboxylation conditions of pressure and temperature comprise total pressures of about 10 to about 80 barg and temperatures of about 150 to about 250° C.

4. Process according to claim 2 wherein the olefin is ethylene or propylene, the onium halide salt is an imidazolium iodide or a pyridinium iodide and the hydrocarboxylation conditions of pressure and temperature comprise total pressures of about 10 to about 80 barg and temperatures of about 150 to about 250 C.

5. Process comprising the steps of:
(a) feeding to a reaction zone (I) an olefin, (ii) water, (iii) a Group VIII metal hydrocarboxylation catalyst, (iv) an onium halide salt compound and, optionally, an inert solvent to provide a reaction zone liquid and feeding carbon monoxide to the reaction zone liquid under hydrocarboxylation conditions of pressure and temperature; and
(b) removing from the reaction zone a crude liquid product comprising a carboxylic acid, unreacted olefin, water, Group VIII metal hydrocarboxylation catalyst, onium halide salt compound, optional inert solvent and carbon monoxide;
wherein a halide compound, other than the onium halide salt, exogenous or extraneous to the process is not added to the reaction zone.

6. Process according to claim 5 wherein the reaction zone is maintained at a temperature of about 100 to about 250 ° C. and a total pressure of about 5 to about 80 bar gauge.

7. Process according to claim 6 wherein the olefin contains 2 to about 12 carbon atoms, the onium halide salt is a quaternary ammonium iodide or a quaternary phosphonium iodide and the Group VIII metal hydrocarboxylation catalyst is rhodium or a rhodium compound.

8. Process according to claim 7 wherein the olefin is ethylene or propylene, the onium halide salt is an imidazolium iodide or a pyridinium iodide and the hydrocarboxylation conditions of pressure and temperature comprise pressures of about 10 to about 80 barg and temperatures of about 150 to about 250° C.

9. Process according to claim 8 wherein the onium halide salt compound is a 1,3-dialkylimidazolium iodide.

10. Process according to claim 5 which includes the steps of:
(c) refining the crude liquid hydrocarboxylation product to recover (1) carboxylic acid product, (2) a low boiling fraction comprising unreacted olefin and (3) a high boiling fraction comprising Group VIII metal hydrocarboxylation catalyst, onium halide salt compound and optional inert solvent; and
(d) recycling the low boiling and high boiling fraction to the reaction zone.

11. Process comprising the steps of:
(a) feeding (i) an olefin, (ii) water, and (iii) carbon monoxide to a reaction zone containing a solution comprising a Group VIII metal hydrocarboxylation catalyst and an onium halide salt compound to provide a reaction zone liquid maintained under hydrocarboxylation conditions of pressure and temperature wherein the temperature of the reaction zone is maintained above the dew point of carboxylic acid product; and
(b) removing from the reaction zone a crude gaseous product comprising carboxylic acid, olefin, water and carbon monoxide;
wherein a halide compound, other than the onium halide salt, exogenous or extraneous to the process is not added to the reaction zone.

12. Process according to claim 11 wherein the reaction zone is maintained at a temperature of about 120 to about 240° C. and a total pressure of about 1 to about 80 bar gauge.

13. Process according to claim 12 wherein the olefin contains 2 to about 12 carbon atoms, the onium halide salt is a quaternary ammonium iodide or a quaternary phosphonium iodide and the Group VIII metal hydrocarboxylation catalyst is rhodium or a rhodium compound.

14. Process according to claim 13 wherein the olefin is ethylene or propylene, the onium halide salt is an imidazolium iodide or a pyridinium iodide and the hydrocarboxylation conditions of pressure and temperature comprise total pressures of about 10 to about 50 barg and temperatures of about 150 to about 240° C.

15. Process according to claim 14 wherein the onium halide salt compound is a 1,3-dialkylimidazolium iodide.

16. Process according to claim 11 which includes the steps of:

(c) refining the crude gaseous product to recover (1) carboxylic acid product and (2) a low boiling fraction comprising unreacted olefin; and (d) recycling the low boiling fraction to the reaction zone.

* * * * *